United States Patent [19]

Guglielmetti et al.

[11] 4,287,337
[45] Sep. 1, 1981

[54] SPIROPYRAN COMPOUNDS OF PIPERIDINE OR THIAZINE RINGS

[75] Inventors: Robert J. Guglielmetti, Brest; Francis Garnier, Champigny; Yves M. Poirier, Brest; Gisele M. C. Petillon, Briec, all of France

[73] Assignee: Etat Francais represente par le Delegue General pour l'Armement, Paris, France

[21] Appl. No.: 96,395

[22] Filed: Nov. 21, 1979

[30] Foreign Application Priority Data

Nov. 28, 1978 [FR] France .................. 78 33512

[51] Int. Cl.³ ............. C07D 515/10; C07D 491/107
[52] U.S. Cl. ....................... 544/6; 546/17; 546/18; 252/300
[58] Field of Search .............. 544/6; 546/17, 18

[56] References Cited

U.S. PATENT DOCUMENTS 3,320,067  5/1967  Taylor .................. 430/332

OTHER PUBLICATIONS

Maguet et al., J. Heterocyclic Chem. vol. 15, Dec. 1978, pp. 1439-1446.

Primary Examiner—Henry R. Jiles
Assistant Examiner—Bernard Dentz
Attorney, Agent, or Firm—Stevens, Davis, Miller & Mosher

[57] ABSTRACT

The invention relates to spiropyran compounds. They have the general formula (I):

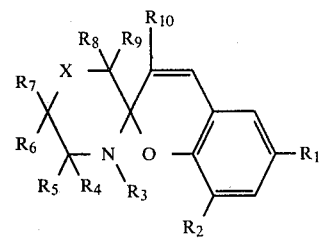

in which:

X represents the $CH_2$ group or a sulfur atom; $R_1$ and $R_2$ represent electron donor and/or acceptor groups selected for instance from the group $NO_2$, $COC_6H_5$, CN, the halogens, the acyl substituents, alkoxy substituents, the hydrogen atom, the alkyl and mercaptoalkyl groups, the ethers of the formula $CH_2OR$, thioethers of the formula $CH_2SR$ and amines of the formula $CH_2NR_2$ in which R represents an alkyl group; $R_3$ is a linear or branched alkyl group, having 1 to 18 carbon atoms, or an arylalkyl or alkenyl group.

—$R_4, R_5, R_6, R_7, R_8$ and $R_9$ have one of the meanings indicated for $R_3$ or represent, two by two, with the group in ortho position, a —$(CH_2)_n$— group in which n is a number between 5 and 10.

$R_{10}$ represents a hydrogen atom if X=S and if X=$CH_2$ a hydrogen atom, an alkyl group having 1 to 18 carbon atoms, an arylalkyl group in which the alkyl group has 1 to 5 carbon atoms, or an alkenyl group having 2 to 10 carbon atoms.

The compounds in accordance with the invention have photochromic properties and are suitable for the recording of information on transparent or opaque supports.

6 Claims, No Drawings

SPIROPYRAN COMPOUNDS OF PIPERIDINE OR THIAZINE RINGS

The technical field of the present invention is that of spiropyran compounds which can be used in the recording of information, in particular by optical or thermal means.

A number of spiropyran compounds which have photochromic properties have been proposed in the literature and it is known that these compounds are transformed into colored merocyanines under the action of photons.

In French Pat. No. 2 008 056 for instance, there have been proposed indoline spiropyrans which can be used for color photography with a support formed of polyvinyl acetate and the absorption maximum of which is located around 570 nm.

In French Pat. No. 2 105 021, there are described benzothiazoline spiropyran derivatives having photochromic properties within a wavelength range extending from 215 to 350 nm.

The Compte Rendu de l'Academie des Sciences de Paris A.282 (May 17, 1976) discloses 2.4.5.6 tetrahydro-1,3-oxazine spiropyrans having photochromic properties. However, no absorption wavelength is indicated.

The object of the present invention is to provide the man skilled in the art with new compounds having remarkable photochromic properties and whose spectrokinetic properties are more advantageous than those of the prior-art compounds.

The object of the invention is new spiropyran compounds characterized by the fact that they have the general formula (I)

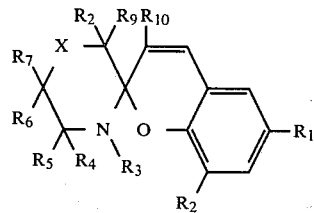

in which:

X represents the $CH_2$ group or a sulfur atom, $R_1$ and $R_2$ represent electron acceptor and/or donor groups, $R_3$ is a linear or branched alkyl group having from 1 to 18 carbon atoms, an arylalkyl group in which the linear or branched alkyl group contains from 1 to 5 carbon atoms, or an alkenyl group having from 2 to 10 carbon atoms;

$R_4, R_5, R_6, R_7, R_8$ and $R_9$ have any of the meanings indicated for $R_3$, represent a hydrogen atom or participate two by two in the formation of a saturated homocycle of 5 to 10 carbon atoms, either with the group present on the same carbon atom or with the group in ortho position.

$R_{10}$ represents a hydrogen atom if $X=S$ while if $X=CH_2$ it represents a hydrogen atom, an alkyl group having 1 to 18 carbon atoms, an arylalkyl group in which the alkyl group contains 1 to 5 carbon atoms, an alkenyl group having 2 to 10 carbon atoms.

The following characteristics may be employed, separately or in combination:

$R_1$ and $R_2$ are selected from the group consisting of $NO_2$, $-COC_6H_5$, $-CN$, the halogens, the acyl substituents, the alkoxy substituents, the hydrogen atom, the alkyl or mercaptoalkyl groups, the ethers of formula $-CH_2OR$, thioethers of formula $CH_2SR$ and amines of formula $-CH_2NR_2$ in which R represents an alkyl group; $R_3$ is selected from among the methyl, ethyl, isopropyl, n-butyl, benzyl or phenethyl substituents; $R_4, R_5, R_6, R_7, R_8$ and $R_9$ have one of the meanings indicated for $R_3$, or represent, two by two, together with the group in ortho position a—$(CH_2)_n$— group in which n is a number between 5 and 10, or a hydrogen atom;

$R_{10}$ represents a hydrogen atom if $X=S$ and if $X=CH_2$ it represents a hydrogen atom or a lower alkyl substituent.

$R_1$ is represented by $NO_2$, $OCH_3$, $COC_6H_5$, I or Br; $R_2$ is represented by $OCH_3$, $NO_2$, H, I or Br; $R_3$ to $R_9$ are represented by a hydrogen atom or a methyl, ethyl, isopropyl, n-butyl, benzyl or phenethyl group and $R_{10}$ represents a hydrogen atom if $X=S$ and if $X=CH_2$ it represents a hydrogen atom or a lower alkyl substituent.

$R_3$ is represented by a methyl, ethyl or isopropyl group; $R_4$ to $R_9$ are selected from the group consisting of hydrogen and the methyl, ethyl and isopropyl groups.

X represents $CH_2$, $R_4$ and $R_5$ hydrogen atoms, and $R_8$ and $R_9$ methyl substituents and $R_{10}$ a methyl or ethyl substituent.

X represents a sulfur atom, $R_6$ and $R_7$ hydrogen atoms and $R_8$ and $R_9$ methyl substituents and $R_{10}$ hydrogen.

The invention also concerns a method of preparing spiropyran derivatives, characterized by the fact that it comprises condensing an orthohydroxy aromatic aldehyde of formula (III):

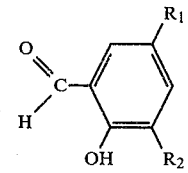

with a quaternary salt of formula (IV):

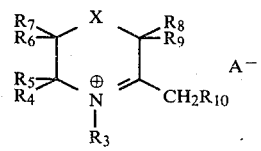

in which X and $R_1$ to $R_{10}$ have the meanings previously indicated and $A^-$ represents an anion selected from the group consisting of iodide, tosylate and methylsulfate anions.

The condensation is preferably carried out in basic medium.

The quaternary salt of formula (IV) is obtained by reacting an alkylation agent of formula (V) with a base of formula (VI) in accordance with the reaction:

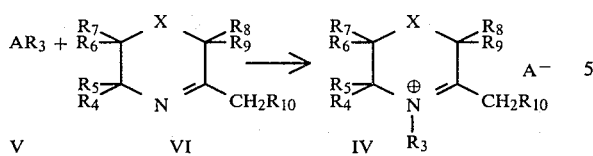

in which $R_3$ to $R_{10}$, X and A have the meanings indicated above.

In order to obtain the products in which X represents the $CH_2$ group, Δ1-piperideine of formula (VI) is prepared by condensation of $LiCH_2R_{10}$ with an ω-halonitrile of formula VIII in accordance with the equation:

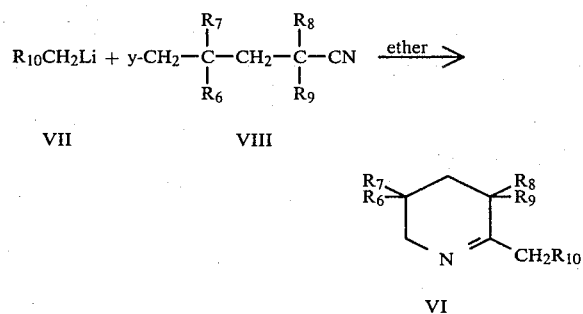

the groups $R_6$ to $R_{10}$ having the meanings indicated.

In order to obtain products in which X represents a sulfur atom, a mercaptoketone of formula (IX) is reacted with an aziridine of formula (X), in accordance with the equation:

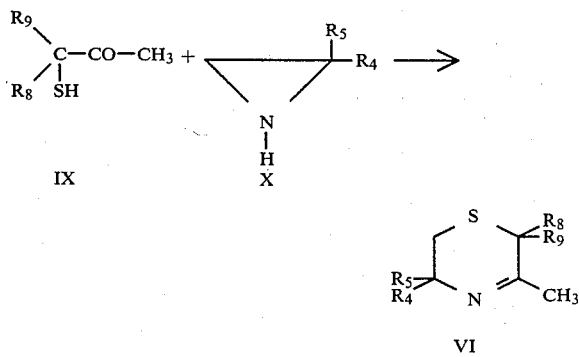

$R_4, R_5, R_8$ and $R_9$ having the meanings indicated above.

The invention also relates to the production of photochromic compositions having at least one spiropyran compound of formula (I).

The compounds of formula I can be obtained in a form different from that indicated. In particular, they may correspond to a so called open form having formula (II).

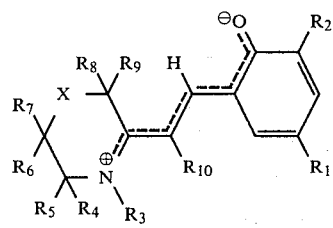

Under the action of photons, the compounds of formula (I) are transformed into colored photomerocyanines of formula (II) which, by heat treatment, will be transformed again into the initial closed form.

The products in accordance with the invention are particularly suitable for the recording of information optically; they may be used on transparent or opaque supports for the recording of stabilized data.

In order to prepare the compounds of the invention, one preferably proceeds in the presence of a solvent consisting for instance of an aliphatic alcohol or else benzene.

In order to obtain the products of the invention in given form, open or else closed, it may be necessary to operate in the presence of a vigorous desiccating agent, such as anhydrous magnesium sulfate.

In order to make the medium basic, one has recourse preferably to piperidine or to a nitrogen base of similar force.

In order to effect the desired condensation, the reaction medium is brought to a temperature between at least 60° C. and the boiling point of the solvent used. One preferably operates at this last mentioned temperature.

In order to isolate the spiropyran, it is advantageous to carry out column chromatography. The absorbent may consist of a silica or alumina gel of 0 to 10% water, in particular, 4 to 10%. As eluant an aromatic organic solvent such as benzene or toluene is used.

Of course, the condensation may be carried out with an aldehyde of formula (III) having the substituents $R_1$ and $R_2$ as defined, among which the conventional groups $NO_2$ and $OCH_3$ are preferred.

The quaternary salt of formula (IV) used in the condensation step is obtained by reacting an alkylation agent of formula (V) with a base of formula (VI).

This quaternization reaction can be carried out with or without solvent, preferably at a temperature between about room temperature and the boiling point of the alkylation agent.

When operating in a solvent, the temperature is between room temperature and the reflux temperature of the solvent. This solvent may be selected from among ethers.

The following examples illustrate the preparation of a number of compounds according to the invention, which takes place in three synthesis steps:

(a) preparation of the 3,4,5,6-tetrahydropyridine and 2H-5,6-dihydro-1,4-thiazine.

(b) quaternization reaction with an alkylation agent.

(c) condensation of the quaternary salt thus obtained with an orthohydroxy aldehyde.

I—Spiropyran compositions in which $X = CH_2$.

EXAMPLE 1

Synthesis of spiropyran of formula (XI)

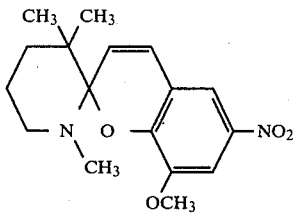

(a) To 15 g of 5-chloro-2,2-dimethylpentane nitrile, diluted in 60 ml of anhydrous ether, there is added drop by drop 0.1 mol of methyl lithium in solution in 200 ml of anhydrous ether, in an inert atomsphere (nitrogen or argon). The reaction medium is maintained between 0° and 5° C. during the addition and for an additional 30 minutes and then at room temperature for 4 hours. After hydrolysis, the 2,3,3-trimethyl-3,4,5,6-tetrahydropyridine is extracted with ether. This compound is then isolated by distillation. A colorless liquid is obtained, $B.P._{14}=60°$ C.; the yield of Δ1-piperideine is 76%.

(b) To the Δ1-piperideine previously obtained an excess of methyl iodide is added; at ordinary temperature the reaction is rather violent. After 8 hours at rest, the salt formed is washed with anhydrous ether. Hygroscopic yellowish crystals are obtained; the yield is quantitative.

(c) 5.34 g ($2 \times 10^{-2}$ mol) of the previous salt and 3.94 g ($2 \times 10^{-2}$ mol) of 3-methoxy-5-nitro-salicylaldehyde are dissolved in 100 cc of anhydrous benzene. 2 cc of piperidine are added and the resultant dark red solution is refluxed for an hour and a half. The benzene solution is chromatographed on alumina with 10% water (eluant: benzene); a solid is withdrawn from the top fraction and purified by recrystallization in ethanol. The yellowish crystals obtained are of a melting point of 127° C. and a yield of 60%.

EXAMPLE 2

Synthesis of spiropyran of formula (XII)

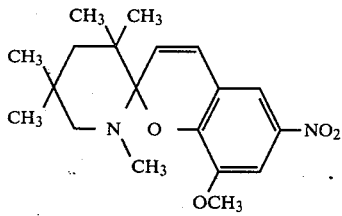

(a) To 22 g of 5-bromo-2,2,4,4-tetramethyl pentane nitrile in 60 ml of anhydrous ether, 0.1 mol of methyl lithium in solution in 200 ml of anhydrous ether is added drop by drop in an inert atmosphere. The reaction medium is maintained between 0° and 5° C. during the addition and then for an additional 30 minutes and then kept at room temperature for 4 hours. After hydrolysis, the aqueous phase is extracted with ether. The 2,3,3,5,5-pentamethyl-3,4,5,6-tetrahydropyridine is then isolated by distillation. There is obtained a colorless liquid of $B.P._{10^{-2}}=43°$ C. in a yield of 70% of Δ1-piperideine.

(b) To the Δ1-piperideine obtained above, an excess of methyl iodide is added. After setting aside overnight, a small amount of anhydrous ether is added to the reaction mixture and the salt crystals thus precipitated. They are slightly brown in color and hygroscopic; the yield is quantitative.

(c) 2.95 g ($10^{-2}$ mol) of the previous salt and 1.97 g ($10^{-2}$ mol) of 3-methoxy-5-nitro-salicylaldehyde are dissolved in 100 cc of anhydrous benzene. 1 cc of piperidine is added and refluxing effected for one hour and 30 minutes. A dark red solution is chromatographed over alumina with 10% water (eluant: benzene); from the top fraction there is removed a solid which is purified by recrystallization in ethanol. Yellow crystals of $M.P.=102°$ C. are obtained in a yield of 45%.

EXAMPLE 3

Synthesis of spiropyran of formula (XIII)

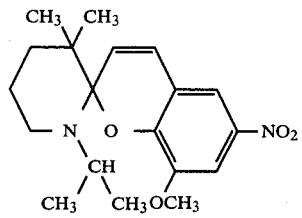

(a) 0.1 mol of methyl lithium dissolved in 200 ml of ether anhydride is added drop by drop in an inert atmosphere (argon or nitrogen) to 15 g of 5-chloro-2,2-dimethyl pentane nitrile diluted in 60 ml of anhydrous ether. The reaction mixture is maintained between 0° and 5° C. during the addition and then for a further 30 minutes and then kept at room temperature for 4 hours. After hydrolysis it is extracted with ether. The 2,3,3-trimethyl-3,4,5,6-tetrahydropyridine is then isolated by distillation. A colorless liquid of $B.P._{14}=60°$ C. is obtained in a yield of 76% of 1-piperideine.

(b) To the Δ1-piperideine thus obtained, an excess of isopropyl iodide is added and it is refluxed for 4 hours. It is then set aside at room temperature; a small amount of ether dried over sodium is then added and the yellowish crystals formed are isolated and kept in a desiccator over phosphoric anhydride. The yield is quantitative.

(c) 2.951 g ($10^{-2}$ mol) of the preceding salt and 1.97 g ($10^{-2}$ mol) of 3-methoxy-5-nitro-salicylaldehyde are dissolved in 100 cc of anhydrous benzene. 1 cc of piperidine is added and refluxing is effected for one and one half hours. The resultant benzene solution is chromatographed over alumina with 10% water (eluant: benzene). The top fraction is a solid which is purified by recrystallization from ethanol. There are obtained crystals of M.P.: 123° C. in a yield of 55%.

EXAMPLE 4

Synthesis of spiropyran of formula (XIV)

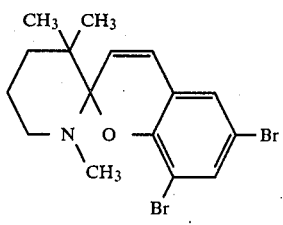

(a) 0.1 mol of methyl lithium dissolved in 200 ml of anhydrous ether is added drop by drop in an inert atmosphere to 15 g of 5-chloro-2,2-dimethyl-pentane-nitrile, dissolved in 60 ml of anhydrous ether. The reaction medium is kept between 0° and 5° C. during the addition and then for an additional 30 minutes, whereupon it is maintained at room temperature for four hours. After hydrolysis, the 2,3,3-trimethyl-3,4,5,6-tetrahydropyridine is extracted with ether. This compound is then isolated by distillation. There is obtained a colorless liquid of B.P.$_{14}$=60° C. in a yield of 76% of Δ1piperideine.

(b) To the Δ1-piperideine thus obtained, an excess of methyl iodide is added; at room temperature the reaction is rather violent. After setting aside for 8 hours, the salt formed is washed with anhydrous ether. Yellowish crystals are obtained; the yield is quantitative.

(c) 5.34 g ($2 \times 10^{-2}$ mol) of the preceding salt and 5.60 g ($2 \times 10^{-2}$ mol) of 3,5-dibromo-salicylaldehyde are dissolved in 100 cc of anhydrous benzene. 2 cc of piperidine are added and refluxing is effected for one and a half hours. The benzene solution is chromatographed over alumina with 10% water (eluant: benzene); from the top fraction there is removed a solid which is purified by recrystallization from a mixture of ethanol and benzene. White crystals are obtained of M.P.=128° C. in a yield of 50%.

EXAMPLE 5

Synthesis of spiropyran of formula (XV)

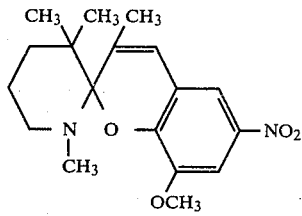

(a) 0.1 mol of ethyl lithium dissolved in 200 ml of anhydrous ether is added drop by drop in an inert atmosphere (nitrogen or argon) to 15 g of 5-chloro-2,2-dimethyl-pentane-nitrile diluted in 60 ml of anhydrous ether. The reaction mixture is held between 0° and 5° C. during the addition and then for an additional 30 minutes and then at room temperature for 4 hours. After hydrolysis, the 3,3-dimethyl-2-ethyl-3,4,5,6-tetrahydropyridine is extracted with ether. This compound is then isolated by distillation. There is obtained a colorless liquid B.P.$_{14}$=66° C. in a yield of Δ1 piperideine of 65%.

(b) To the Δ1-piperideine previously obtained an excess of methyl iodide is added; at ordinary temperature the reaction is rather violent. After setting aside for 8 hours, the salt formed is washed with anhydrous ether. Hygroscopic crystals are obtained; the yield is quantitative.

(c) 5.62 g ($2 \times 10^{-2}$ mol) of the preceding salt and 3.94 g ($2 \times 10^{-2}$ mol) of 3-methoxy-5-nitro-salicylaldehyde are dissolved in 100 cc of anhydrous benzene. 2 cc of piperidine are added and the dark red solution obtained is refluxed for an hour and a half. The benzene solution is chromatographed over alumina with 10% water (eluant: benzene); from the top fraction there is recovered a solid which is purified by recrystallization from ethanol. Yellow crystals are obtained of M.P.=156° C. in a yield of 10%.

EXAMPLE 6

Synthesis of spiropyran of formula (XVI)

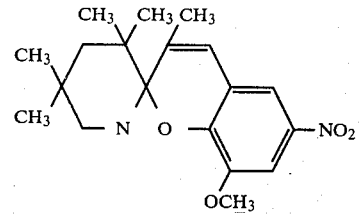

(a) 0.1 mol of ethyl lithium dissolved in 200 ml of anhydrous ether is added drop by drop in an inert atmosphere to 22 g of 5-bromo-2,2,4,4-tetramethyl-pentane nitrile in 60 ml of anhydrous ether. This reaction medium is maintained between 0° and 5° C. during the addition and then for an additional 30 minutes and then is kept at room temperature for 4 hours. After hydrolysis, the aqueous phase is extracted with ether. The 3,3,5,5 tetramethyl-2-ethyl-3,4,5,6-tetrahydropyridine is then isolated by distillation. A colorless liquid of B.P.$_{2.10^{-2}}$=40° C. is obtained in a yield of 40%.

(b) An excess of methyl iodide is added to the Δ1-piperideine obtained above. After setting aside overnight, a small amount of anhydrous ether is added to the reaction medium and the salt crystals thus precipitated. They are slightly brown in color and hygroscopic; the yield is quantitative.

(c) 3.09 g ($10^{-2}$ mol) of the preceding salt and 1.97 g ($10^{-2}$ mol) of 3-methoxy-5-nitro-salicylaldehyde are dissolved in 100 cc of anhydrous benzene. 1 cc of piperidine is added and refluxing is effected for one and one half hours. The dark red solution is chromatographed over alumina with 10% water (eluant: benzene) and there is obtained from the top fraction a solid which is purified by recrystallization in ethanol. Yellow crystals are obtained of M.P.=122° C. in a yield of 14%.

Table 1: Spiropyrans of general formula Ia.

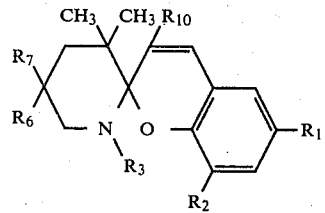

By operating in accordance with Examples 1 to 6, there are obtained spiropyran compounds of structures Ia above in which X represents a CH$_2$ group, R$_4$ and R$_5$ hydrogens, and R$_8$ and R$_9$ methyl groups. Examples 7 to 17 are combined in Table I; the R$_1$,R$_2$,R$_3$,R$_6$,R$_7$ and R$_{10}$ groups present in the compounds of formula I have the meaning indicated.

TABLE 1

| EXAMPLES | R$_1$ | R$_2$ | R$_3$ | R$_6$ | R$_7$ | R$_{10}$ | M.P. (°C.) | Yield (%) |
|---|---|---|---|---|---|---|---|---|
| 7 | NO$_2$ | OCH$_3$ | CH$_3$ | CH$_3$ | H | H | 125 | 60 |
| 8 | NO$_2$ | OCH$_3$ | C$_2$H$_5$ | H | H | H | 114 | 60 |

TABLE 1-continued

| EXAMPLES | R₁ | R₂ | R₃ | R₆ | R₇ | R₁₀ | M.P. (°C.) | Yield (%) |
|---|---|---|---|---|---|---|---|---|
| 9 | NO₂ | OCH₃ | CH₂C₆H₅ | H | H | H | 141 | 35 |
| 10 | OCH₃ | NO₂ | CH₃ | H | H | H | 68 | 62 |
| 11 | I | I | CH₃ | H | H | H | 83 | 50 |
| 12 | —C(=O)—C₆H₅ | H | CH₃ | H | H | H | non-crystallized | 55 |
| 13 | NO₂ | NO₂ | CH₃ | H | H | H | 137 | 12,5 |
| 14 | NO₂ | H | CH₃ | H | H | H | 117 | 22 |
| 15 | H | H | CH₃ | H | H | H | Viscous liquid | 28 |
| 16 | NO₂ | OCH₃ | CH₃ | H | CH₃ | CH₃ | 100 | 5 |
| 17 | NO₂ | OCH₃ | CH₃ | H | H | C₂H₅ | 127 | 8 |

II—Spiropyran compounds in which X=S(R₁₀=H)

EXAMPLE 18

Synthesis of spiropyran of formula (XVII)

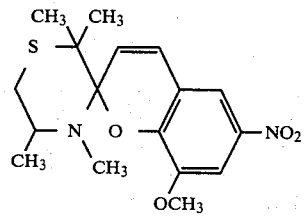
XVII (a) 33 g (0.58 mol) of 2-methyl-aziridine and 1 sodium pellet are heated in a nitrogen atmosphere in a round bottom flask at 40° C. on a water bath. 59 g (0.5 mol) of 3-mercapto-3-methyl butanone are then added drop by drop.

After the completion of the addition, the mixture is heated for one hour at 60° C. After washing and extraction, the 2,2,3,5 tetramethyl 2H-5, 6-dihydro-1, 4-thiazine is isolated by distillation. A liquid of B.P.$_{5.10-2}$=37° C. is obtained in a yield of 95%.

(b) To 3.14 g of 1,4-thiazine an excess of methyl iodide is added. The quaternization is allowed to take place overnight at room temperature. White crystals are obtained after washing with anhydrous ether. The yield is substantially quantitative.

(c) 5.98 g (2×10⁻² mol) of the preceding salt and 3.94 g (2×10⁻² mol) of 3-methoxy-5-nitro-salicylaldehyde are dissolved in anhydrous benzene. 2 cc of piperidine are added and refluxing is effected for one hour; during the refluxing the benzene is dried over magnesium sulfate. The benzene solution is chromatographed over 10% alumina (eluant: benzene). The yellow top fraction is evaporated and a solid isolated which is crystallized from ethanol. Yellow crystals of M.P.=126° C. are obtained in a yield of 36%.

EXAMPLE 19

Synthesis of spiropyran of formula (XVIII)

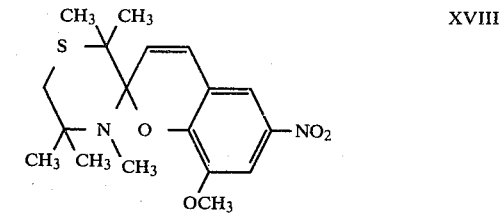
XVIII (a) 20.6 g (0.29 mol) of 2,2-dimethyl aziridine and 1 sodium hydroxide pellet are heated in a round bottom flask in a nitrogen atmosphere at 40° C. on a water bath. Thereupon 29.5 g (0.25 mol) of 3-mercapto-3methyl butanone are added drop by drop. The mixture is then heated at 60° C. for one hour. After washing and extraction, the 2,2,3,5,5-pentamethyl 2H-5,6-dihydro-1,4-thiazine is distilled. A colorless liquid of B.P.$_{0.6}$=45° C. is obtained in a yield of 68%.

(b) An excess of methyl iodide is added to the thiazine thus obtained. It is set aside at room temperature for 2 to 3 days. White crystals are obtained in quantitative yield.

(c) 6.2 g (2×10⁻² mol) of the preceding salt and 3.94 g of 3-methoxy-5-nitro salicylaldehyde are dissolved in 100 cc of anhydrous benzene. 2 cc of piperidine are added, and the reaction mixture is refluxed for an hour and a half; the benzene is dried during the reaction over magnesium sulfate. The benzene solution is chromatographed over alumina with 10% water (eluant: benzene). From the pale yellow fraction there is obtained a solid which is purified by recrystallization from ethanol. Yellow crystals of M.P.=168° C. are obtained in a yield of 29%.

EXAMPLE 20

Synthesis of the spiropyran of formula (XIX)

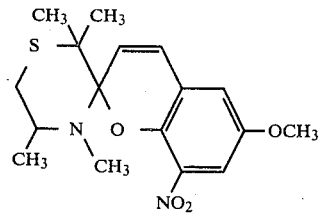
XIX (a) 33 g (0.58 mol) of 2-methyl aziridine and 1 pellet of sodium hydroxide are heated under a nitrogen atmosphere on a water bath at 40° C. in a round bottom flask. Thereupon 59 g (0.5 mol) of 3-mercapto-3-methyl butanone are added. At the end of the addition, the mixture is heated at 60° C. for one hour. After washing and extraction, the 2,2,3,5-tetramethyl 2H-5,6-dihydro-1,4-thiazine is distilled. A liquid of $B.P._{5 \times 10^{-2}} = 37°$ C. is obtained in a yield of 95%.

(b) An excess of methyl iodine is added to the 1,4-thiazine thus obtained. The quaternization is carried out overnight at room temperature. White crystals are obtained after washing in anhydrous ether. The yield is substantially quantitative.

(c) 5.98 g ($2 \times 10^{-2}$ mol) of quaternary salt and 3.94 g ($2 \times 10^{-2}$ mol) of 5-methoxy-3-nitro salicylaldehyde are dissolved in 100 cc of anhydrous benzene. 2 cc of piperidine are added and refluxing is effected for 20 minutes. The benzene solution is chromatographed over alumina with 10% water. The top fraction is evaporated and a solid isolated which is purified by recrystallization from ethanol. Lemon yellow crystals of M.P.=116° C. are obtained in a yield of 48%.

EXAMPLE 21

Synthesis of the spiropyran of formula (XX)

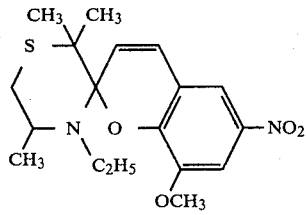

(a) 33 g (0.58 mol) of 2-methyl aziridine and 1 sodium hydroxide pellet are heated in an inert atmosphere on a water bath at 40° C. in a round bottom flask. Thereupon 59 g (0.5 mol) of 3-mercapto-3-methyl butanone are added drop by drop. At the end of the addition, the mixture is heated at 60° C. for one hour. After washing and extraction, the 2,2,3,5-tetramethyl 2H-5,6-dihydro-1,4-thiazine is extracted; liquid $B.P._{5 \times 10^{-2}} = 37°$ C.; yield 95%.

(b) To the 1,4-thiazine thus obtained, an excess of ethyl iodide is added and refluxed for 4 hours. It is then set aside at room temperature. After washing with acetone, hygroscopic white crystals are obtained. The yield is substantially quantitative.

(c) 6.26 g ($2 \times 10^{-2}$ mol) of the preceding salt and 3.94 g of 3-methoxy-5-nitro salicylaldehyde are dissolved in 100 cc of anhydrous benzene. 2 cc of piperidine are added and the mixture is refluxed for 15 minutes; the benzene is dried over magnesium sulfate during the course of the reaction. The benzene solution is chromatogaphed over alumina with 10% water (eluant: benzene). The orangish-red top fraction is evaporated; the spiropyran is isolated in the form of a brown lake which is obtained in a yield of 58%.

By operating in the manner set forth in Examples 18 to 21 spiropyran compounds are prepared having the formula (Ib) below in which $R_6 = R_7 = H$, $R_8 = R_9 = CH_3$; the groups $R_1$ to $R_5$ have the meaning indicated below.

TABLE 2

Spiropyrans of general formula (Ib).

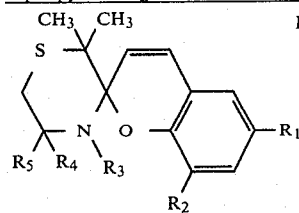

| EX. | $R_1$ | $R_2$ | $R_3$ | $R_4$ | $R_5$ | M.P. (°C.) | YIELD % |
|---|---|---|---|---|---|---|---|
| 22 | I | I | $CH_3$ | $CH_3$ | H | 132 | 42 |
| 23 | Br | Br | $CH_3$ | $CH_3$ | H | 119 | 72 |
| 24 | CO—$C_6H_5$ | H | $CH_3$ | $CH_3$ | H | non-crystallized | 51 |
| 25 | $NO_2$ | $NO_2$ | $CH_3$ | $CH_3$ | H | 119 | 1 |
| 26 | $NO_2$ | $OCH_3$ | $iC_3H_7$ | $CH_3$ | H | lake | 44 |

As indicated previously, the derivatives in accordance with the invention have photochromic properties.

In order to study these properties the flash photolysis technique was employed and the change in absorbance of the absorption maximum of the colored form and the kinetic thermal discoloration constant of spiropyran solutions in anhydrous toluene (20 ppm of water) were measured. These measurements were carried out at 25° C. in cells of a length of 10 cm. and a thickness of 3 cm. and with a constant photolysis energy of 800 joules (with a spread spectrum). The solvent used is toluene and the concentration of the sample is $5 \times 10^{-5}$ mol/l.

Two photographic recordings make it possible to determine the spectral and kinetic characteristics during the discoloration of the photochromic sample.

In table 3 below there are set forth the results obtained with a number of compounds in accordance with the invention. In this table there are indicatd the values of the initial absorbance $A_0$ at the time of the photolysis, the thermal discoloration constant $K\Delta$ in $S^{-1}$ as well as the value $\lambda$ of the open form, measured for the compounds obtained in accordance with Examples 1 to 20, 22 to 25.

TABLE 3

| EXAMPLES | λ (nm) O.F. | Ao | K in $s^{-1}$ (25° C.) |
|---|---|---|---|
| 1 | 580 | 1,42 | 0,42 |
| 2 | 580 | 1,68 | 0,36 |
| 3 | 530 | 0,66 | 0,17 |
| 4 | 580 | 0,05 | 5,6 |
| 5 | 430 | 0,125 | 0,46 |
| 6 | 428 | 0,715 | 0,32 |
| 7 | 580 | 1,68 | 0,35 |
| 8 | 530 | 1,18 | 0,15 |
| 9 | 530 | 0,73 | 0,60 |
| 10 | 600 | 0,07 | 23 |
| 11 | 580 | 0,03 | 8,5 |
| 12 | 580 | 1,24 | 0,73 |
| 13 | 530 | 0,27 | 0,014 |
| 14 | 580 | 0,30 | 0,02 |
| 15 | 560 | 0,02 | 59 |
| 16 | 436 | 0,57 | 0,15 |
| 17 | 420 | 0,172 | 0,23 |
| 18 | 600 | 1,22 | 75 |
| 19 | 590 | 1,40 | 50 |
| 20 | 620 | 0,09 | 171 |
| 22 | 600 | 0,08 | 147 |
| 23 | 600 | 0,03 | 106 |
| 24 | 600 | 0,24 | 160 |

TABLE 3-continued

| EXAMPLES | λ (nm) O.F. | Ao | K in s$^{-1}$ (25° C.) |
|---|---|---|---|
| 25 | 560 | 0,76 | 19,5 |

In Table 4 there are set forth the values obtained under the same operating conditions for a number of indoline compounds of the prior art having the following general formula:

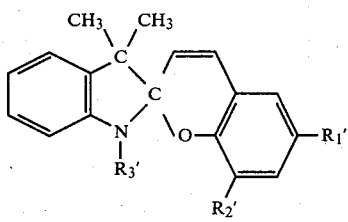

TABLE 4

| $R_1'$ | $R_2'$ | $R_3'$ | λ (nm) O.F. | Ao | $k_A$ (s$^{-1}$) |
|---|---|---|---|---|---|
| NO$_2$ | OCH$_3$ | CH$_3$ | 620 | 1,0 | 2,3.10$^{-2}$ |
| OCH$_3$ | NO$_2$ | CH$_3$ | 640 | 0,30 | 8,9.10$^{-1}$ |
| NO$_2$ | H | CH$_3$ | 620 | 0,78 | 2,3.10$^{-1}$ |
| CO—C$_6$H$_5$ | H | C$_6$H$_5$ | 620 | 0,72 | 2,32 |
| I | I | CH$_3$ | 620 | 0,12 | 0,11 |
| Br | Br | CH$_3$ | 620 | 0,05 | 0,143 |
| H | H | CH$_3$ | 580 | — | 0,95 |

In Table 5, there are set forth the values obtained under the smae operating conditions for a number of known benzothiazoline compounds having the general formula:

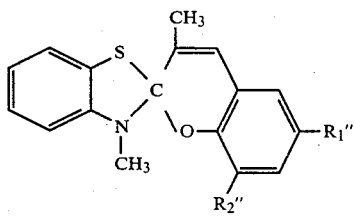

TABLE 5

| $R_1''$ | $R_2''$ | λ (nm) O.F. | Ao | $K_{66}$ (s$^{-1}$) |
|---|---|---|---|---|
| NO$_2$ | OCH$_3$ | 620 | 0,25 | 2,6 |
| OCH$_3$ | NO$_2$ | 645 | 0,04 | 30,35 |
| NO$_2$ | H | 580 | 0,06 | 1,3 |
| COC$_6$H$_5$ | H | — | slightly colored | 0,136 |

The same measurements were also carried out with respect to a 1,3-thiazine compound of the formula:

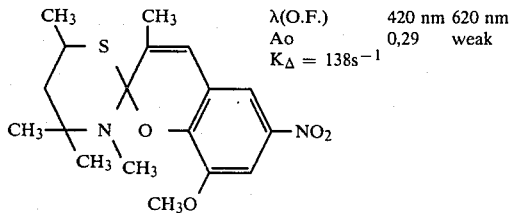

λ(O.F.)   420 nm  620 nm
Ao         0,29   weak
$K_A = 138 s^{-1}$

A comparison of the results obtained for the compounds in accordance with the invention and the prior-art compounds shows a remarkable capability of the former to become colored, increasing their range of use both at the kinetic level and at the spectroscopic level.

Mention should be made of the entirely remarkable spectroscopic properties of the piperidine compounds in which $R_{10}$ is represented by a methyl or ethyl group. These compounds have a single absorption band at about 420 nm, that is to say, they absorb in the blue and become yellow under the photon action. Thus the compounds of the invention make it possible to have access to 3-color photochromic films (yellow, blue and red).

It is also interesting to note that the kinetic constants of thermal discoloration differ in accordance with the nature of the substituents of the compounds in accordance with the invention, which results in a greater stability of the open forms or photomerocyanines of the derivatives studied.

It may be noted in general that the derivatives in accordance with the invention in which X is a CH$_2$ group, $R_1$=NO$_2$ and $R_2$=OCH$_3$ lead to photomerocyanines which are highly stabilized. As a result, they are of particular interest for uses in which it is desired to store information and they are advantageously employed for the recording of stabilized information on transparent supports, for instance, films, or opaque supports such as paper. Thus these derivatives are particularly suitable especially for the reproduction of documents (auto-processor reprography process), for non-conventional photography and for the obtaining of thermally erasable stable latent images. In particular, these derivatives are advantageously used for the production of photochromic films and photochromic papers. The films can be obtained from preparations comprising cellulose acetobutyrate or any other support of plastic material.

In order to produce the photochromic papers, a preparation containing from 1 to 5% by weight of derivative in accordance with the invention, and preferably about 2%, is spread onto paper. Such a preparation advantageously contains from 20 to 80 grams and preferably 40 to 60 grams, of semiconductive substance such as TiO$_2$ or ZnO, from 5 to 25 grams, and preferably 10 to 20 grams, of a binder such as that formed by a resin marketed under the designation RP 1022, from 10 to 40 grams, and preferably 20 to 30 grams, of an organic solvent such as toluene, from 2 to 30 grams, and preferably 5 to 15 grams, of an alcohol such as ethanol, and from 0.5 to 5 grams, and preferably 1 to 3 grams, of spiropyran.

A preferred preparation used in accordance with the invention contains about 50 grams of the said semiconductive substance, about 15 grams of the said binder, about 25 grams of organic solvent, about 10 grams of alcohol and about 2 grams of spiropyran.

By irradiation of the photochromic paper there is obtained a high-contrast, high-resolution image which is stabile for some time. These photochromic films and papers have numerous applications, particularly in the field of artisinal photography, for evaluating neagtives and for the recording of data displayed on a cathode tube.

An examination of Table 3 also shows that the derivatives in accordance with the invention in which X is a sulfur atom, $R_1$=NO$_2$ and $R_2$=OCH$_3$, while having a good ability to become colored, have fast thermal discoloration rates.

Thus these properties make it possible to use the derivatives of this type in applications where the speed of erasure of the information is a determinative factor. This is true for instance of display screens, of control by light of the transparency of a diaphragm, of the treatment of images in correlator systems, and of the recording of images with ultra-violet laser.

We claim:

1. A spiropyran compound having the formula (I)

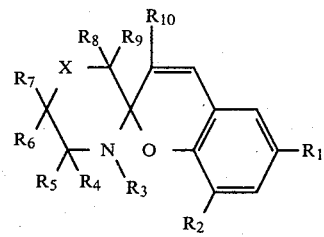

in which:

X represents a $CH_2$ group or a sulfur atom, $R_1$ and $R_2$ are selected from the group consisting of $NO_2$, $-COC_6H_5$, $-CN$, the halogens, the alkoxy substituents, the hydrogen atom, the alkyl and mercaptoalkyl groups, the ethers of formula $-CH_2OR$, thioethers of the formula $CH_2SR$ and amines of the formula $-CH_2NR_2$ in which R represents an alkyl group, $R_3$ is a linear or branched alkyl group comprising from 1 to 18 carbon atoms, a phenylalkl group in which the linear or branched alkyl group has from 1 to 5 carbon atoms, or an alkenyl group having 2 to 10 carbon atoms;

$R_4$, $R_5$, $R_6$, $R_7$, $R_8$ and $R_9$ have one of the meanings indicated for $R_3$, represent a hydrogen atom, or participate, two by two, in the formation of a saturated homocycle of 5 to 10 carbon atoms, either with the group present on the same carbon atom or with the group in ortho position;

$R_{10}$ represents a hydrogen atom if $X=S$ and if $X=CH_2$ a hydrogen atom, an alkyl group having 1 to 18 carbon atoms, a phenylalkyl group in which the alkyl group has 1 to 5 carbon atoms, or an alkenyl group having 2 to 10 carbon atoms.

2. A compound according to claim 1, characterized by the fact that:

$R_1$ and $R_2$ are selected from the group consisting of $NO_2$, $-COC_6H_5$, $-CN$, the halogens, the alkoxy substituents, the hydrogen atom, the alkyl and mercaptoalkyl groups, the ethers of formula $-CH_2OR$, thioethers of the formula $CH_2SR$ and amines of the formula $-CH_2NR_2$ in which R represents an alkyl group.

$R_3$ is selected from among the methyl, ethyl, isopropyl, n-butyl, benzyl or phenethyl substituents;

$R_4$, $R_5$, $R_6$, $R_7$, $R_8$ and $R_9$ have one of the meanings indicated for $R_3$, or represent, two by two, with the group in ortho position, a $-(CH_2)n$ group in which n is a number between 5 and 10 or a hydrogen atom.

$R_{10}$ represents a hydrogen atom if $X=S$ and if $X=CH_2$ a hydrogen atom or a lower alkyl substituent.

3. A compound according to claim 2, characterized by the fact that:

$R_1$ is represented by $NO_2$, $OCH_3$, $-COC_6H_5$, I or Br;
$R_2$ is represented by $OCH_3$, $NO_2$, H, I or Br;
$R_4$ to $R_9$ are represented by a hydrogen atom or a methyl, ethyl, isopropyl, n-butyl, benzyl or phenethyl group;
$R_{10}$ represents a hydrogen atom is $X=S$ and if $X=CH_2$ a hydrogen atom or a lower alkyl substituent.

4. A compound according to claim 3, characterized by the fact that $R_3$ is represented by a methyl, ethyl or isopropyl group and $R_4$ to $R_9$ are selected from the group consisting of hydrogen and the methyl, ethyl, or isopropyl groups.

5. A compound according to any of claims 2 to 4, characterized by the fact that X represents the $CH_2$ group, $R_4$ and $R_5$ represent hydrogen atoms, and $R_8$ and $R_9$ represent methyl substituents and $R_{10}$ is a methyl or ethyl group.

6. A compound according to any of claims 2 to 4, characterized by the fact that X represents a sulfur atom, $R_6$ and $R_7$ hydrogen atoms, and $R_8$ and $R_9$ methyl substituents and $R_{10}$ a hydrogen atom.

* * * * *